(12) United States Patent
Sanchez, Jr.

(10) Patent No.: US 10,238,798 B2
(45) Date of Patent: Mar. 26, 2019

(54) PRESSURIZABLE FLUID SUPPLY APPARATUS

(71) Applicant: Novartis AG, Basel (CH)

(72) Inventor: Robert Joseph Sanchez, Jr., Oceanside, CA (US)

(73) Assignee: Novartis AG, Basel (CH)

( * ) Notice: Subject to any disclaimer, the term of this patent is extended or adjusted under 35 U.S.C. 154(b) by 283 days.

(21) Appl. No.: 15/076,786

(22) Filed: Mar. 22, 2016

(65) Prior Publication Data
US 2017/0274143 A1 Sep. 28, 2017

(51) Int. Cl.
*A61M 5/14* (2006.01)
*A61M 5/155* (2006.01)
*A61F 9/007* (2006.01)
*A61M 5/172* (2006.01)
*A61M 5/168* (2006.01)

(52) U.S. Cl.
CPC .............. *A61M 5/155* (2013.01); *A61F 9/007* (2013.01); *A61M 5/16813* (2013.01); *A61M 5/172* (2013.01); *A61M 2205/505* (2013.01); *A61M 2210/0612* (2013.01)

(58) Field of Classification Search
CPC .......... A61M 5/14586; A61M 5/14593; A61M 5/1483; A61M 5/155; A61M 5/148; A61M 5/16813; A61M 1/1037; A61M 1/1044; A61M 1/1048; A61M 2039/242; F04B 43/073; F04B 43/0733; F04B 43/0072; F04B 43/009; F04B 43/113; F04B 45/0336; F04B 45/064; F04B 45/0736; A61H 9/0078
See application file for complete search history.

(56) References Cited

U.S. PATENT DOCUMENTS

| | | | | |
|---|---|---|---|---|
| 3,880,164 | A * | 4/1975 | Stepno | A61M 1/0066 604/131 |
| 4,237,881 | A * | 12/1980 | Beigler | A61M 5/1483 128/205.13 |
| 4,270,533 | A * | 6/1981 | Andreas | A61J 1/10 128/DIG. 12 |
| 4,735,613 | A * | 4/1988 | Bellin | A61M 5/1483 604/118 |
| 5,071,104 | A * | 12/1991 | Witt | A61M 3/0262 251/342 |
| 5,399,166 | A * | 3/1995 | Laing | A61M 5/1483 604/131 |
| 6,135,989 | A * | 10/2000 | Atad | A61M 5/1483 604/408 |
| 6,558,346 | B1 * | 5/2003 | Yoshioka | A61M 5/14244 604/118 |
| 6,579,223 | B2 * | 6/2003 | Palmer | A61M 1/1062 600/16 |

(Continued)

*Primary Examiner* — Nathan R Price
*Assistant Examiner* — Courtney B Fredrickson (57) ABSTRACT

A pressurizable fluid supply apparatus may include a bag to hold a fluid. The bag may include a fluid outflow interface and a bladder positioned adjacent to the bag. The bladder may include a plurality of chambers positioned vertically in series. Adjacent chambers may be separated by dividers. The dividers may be configured to allow fluid flow between adjacent chambers under specified conditions. The bladder may further include a pressure inlet positioned at a top of the bladder.

14 Claims, 6 Drawing Sheets

(56) References Cited

U.S. PATENT DOCUMENTS

| | | | | |
|---|---|---|---|---|
| 7,066,874 | B2* | 6/2006 | Riebman | A61M 1/107 |
| | | | | 600/16 |
| 2003/0040708 | A1* | 2/2003 | Rogers | A61M 5/148 |
| | | | | 604/135 |
| 2005/0267595 | A1* | 12/2005 | Chen | A61F 5/003 |
| | | | | 623/23.65 |
| 2008/0097323 | A1* | 4/2008 | Robertson | A61J 1/1462 |
| | | | | 604/142 |
| 2014/0276587 | A1* | 9/2014 | Imran | A61M 5/1483 |
| | | | | 604/506 |

* cited by examiner

PRESSURIZABLE FLUID SUPPLY APPARATUS

TECHNICAL FIELD

The present disclosure is directed to methods and systems for performing ophthalmic surgical procedures, and more particularly, to methods and systems for pressurizing and delivering and infusion fluid to a patient's eye.

BACKGROUND

Ophthalmic surgical procedures often involve extracting tissue and fluid from the patient's eye. For example, phacoemulsification involves using ultrasonic energy to break the lens of the eye into small pieces that are promptly aspirated from the lens capsule. Extraction of fluid and other substances from an eye will cause depressurization of that eye, which can cause a number of problems. To counteract these problems, a replacement fluid is simultaneously injected into the eye to keep the pressure within the eye at an acceptable level. In a further example, vitreoretinal surgeries involve the cutting and extracting vitreous fibrils from the eye. During such a procedure, a replacement fluid is also simultaneously supplied to maintain the intraocular pressure at an acceptable level. It is desirable to provide such fluid infusion in a versatile and efficient manner.

SUMMARY

The present disclosure describes examples of pressurizable fluid supply apparatuses usable to supply fluids to a patient undergoing treatment. These apparatuses may include a bladder and a bag. The bag may include a fluid outflow interface. The bladder may be positioned adjacent to the bag. The bladder may include a plurality of chambers positioned vertically in series, adjacent chambers being separated by dividers, the dividers configured to selectively allow fluid flow between adjacent chambers. The bladder may further include a pressure inlet positioned at a top of the bladder.

According to some examples, a fluid delivery system may include a pressure source, a fluid infusion line, and a pressurizable fluid supply apparatus that may include a bag to hold a fluid. The bag may include a fluid outflow interface that is connectable to the fluid infusion line. The pressurizable fluid supply apparatus further includes a bladder positioned adjacent to the bag. The bladder includes a plurality of chambers positioned vertically in series, adjacent chambers being separated by dividers, the dividers configured to allow fluid flow between adjacent chambers. The bladder may include a pressure inlet positioned at a top of the bladder, the pressure inlet being connectable to the pressure source. The fluid delivery system may further include a receptacle adapted to fit the pressurizable fluid supply apparatus.

In additional examples, a method includes connecting a fluid outflow interface of a bag to a fluid infusion line and connecting a pressure inlet of a bladder to a pressure source. The bladder may include a plurality of chambers positioned vertically in series, adjacent chambers being separated by dividers. The dividers may be configured to selectively allow fluid flow between adjacent chambers. The method further includes, with fluid from the pressure source, inflating the bladder such that the bladder presses the bag against a wall to press fluid from the bag into the fluid infusion line.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

The accompanying drawings illustrate embodiments and implementations of the devices and methods disclosed herein and together with the description, serve to explain the principles of the present disclosure.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For simplicity, in some instances the same reference numbers are used throughout the drawings to refer to the same or like parts.

The systems and methods described herein use a pressurizable fluid delivery apparatus that is capable of being used by fluid delivery systems that use fluid-filled bags as a fluid reservoir as well as fluid delivery systems that use fluid-filled bottles as a fluid reservoir. As will be explained in further detail below, a pressurized non-infusion fluid, such as a gas, may be used to induce the flow of an infusion fluid, such as a saline solution, to an ophthalmic surgical tool or a surgical site.

Some fluid delivery systems provide infusion fluid from a fluid-filled bag. In these types of systems, a mechanical actuator mechanism squeezes the bag to push fluid out of the bag and into an infusion line. The infusion line provides fluid communication between the bag and the ophthalmic tool that injects the fluid into the patient's eye. Alternatively, some fluid delivery systems inject fluid into the eye from a fluid-filled bottle. Typically, the bottle has a fluid outflow interface that can be connected to the fluid infusion line. The bottle also has a pressure inlet that is connected to a pressurized fluid source such as a pressurized gas. When the pressurized gas is injected into the top of the bottle, it pushes fluid out of the fluid outflow interface at the bottom of the bottle and into the food infusion line.

According to principles described herein, a pressurizable fluid supply apparatus may be structurally configured to be compatible with fluid delivery systems structurally configured for bottles as well as fluid delivery systems structurally configured for bags. According to one example, the pressurizable fluid supply apparatus includes a bag and a bladder. The bag may include a fluid outflow interface that is connectable to a fluid infusion line of a fluid delivery system. The bladder includes a pressure inlet that is connectable to a pressure source of the fluid delivery system. The bladder is adapted to be disposed adjacent to the bag such that inflation of the bladder puts pressure on the bag, compressing the bag, and forcing fluid out of the bag. The fluid delivery system and the pressurizable fluid supply apparatus will be described in further detail below.

Figure 1:
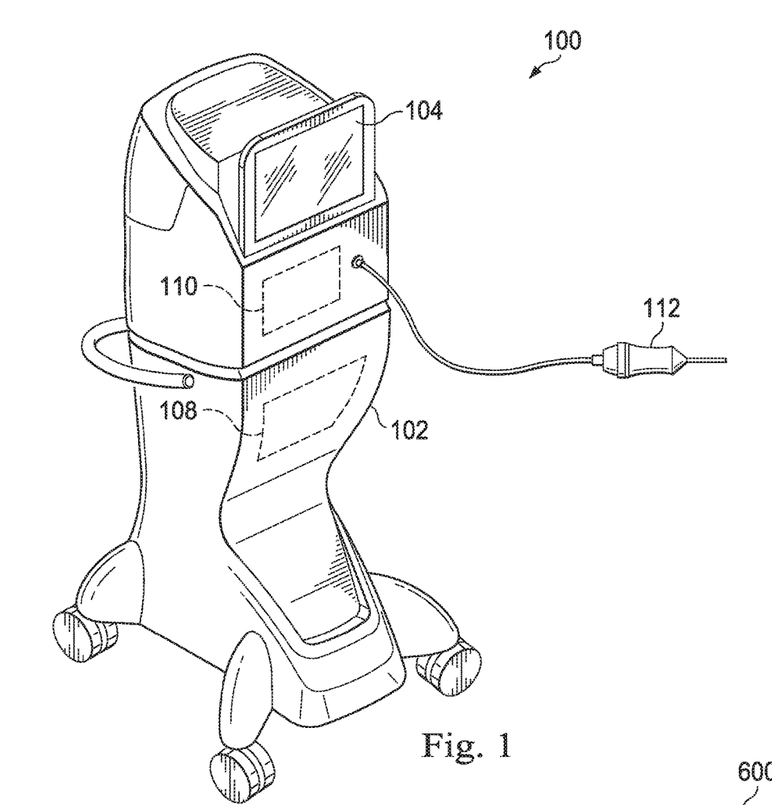
FIG. 1 is a diagram showing an illustrative ophthalmic surgical system that includes a fluid delivery system.

FIG. 1 is a diagram showing an illustrative ophthalmic surgical system 100 that includes a fluid delivery system 110. According to the present example, the ophthalmic surgical system 100 includes a surgical console 102 and an ophthalmic surgical tool 112 such as an infusion tool. The surgical console 102 includes a display screen 104 and the fluid delivery system 110. In one implementation, the surgical console 102 is designed to be mobile and may be used by a user, such as a health care provider, to perform ophthalmic surgical procedures. The surgical console 102 may also include a control system 108 that may be configured to process, receive, and store data to perform various functions associated with the ophthalmic surgical tool 112.

The display screen 104 may communicate information to the user, and in some implementations, may show data relating to system operation and performance during a surgical procedure. In some examples, the display screen 104 is a touchscreen that allows the operator to interact with the surgical console 102 through a graphical user interface.

Figure 2:
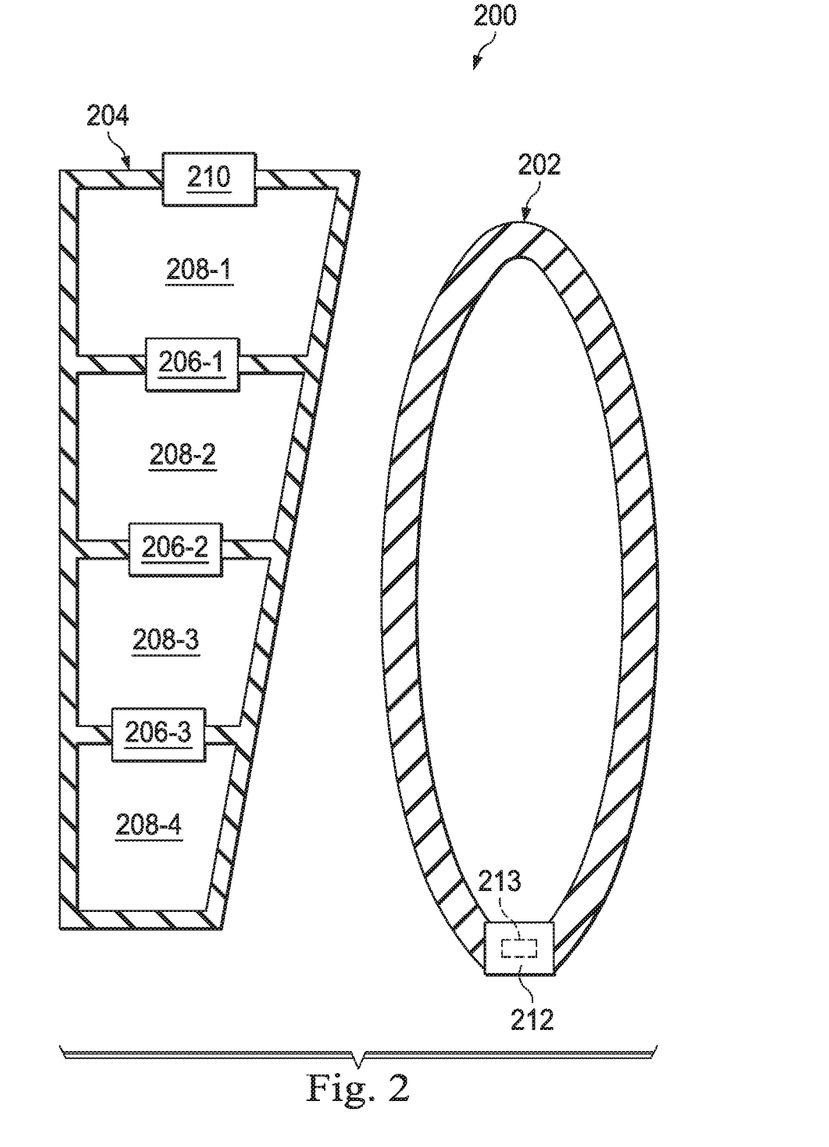
FIG. 2 is a diagram showing an illustrative pressurizable fluid supply apparatus.

FIG. 2 is a diagram showing an illustrative pressurizable fluid supply apparatus 200. The pressurizable fluid supply apparatus 200 includes a bag 202 and a bladder 204. The bag 202 is structurally configured to be filled with an infusion fluid. The bag 202 is also structurally configured to be disposed adjacent to the bladder 204. The bladder 204 is structurally configured to be inflatable from a first volume to a second volume, such that when inflated, it places pressure on the bag 202 to press fluid out of the bag 202.

The bag 202 may be made of a flexible material such as a plastic or polymer. The bag 202 may be filled with a fluid such as a balanced salt solution suitable for injection into a patient's eye. The bag 202 also includes a fluid outflow interface 212 that is connectable to a fluid infusion line (not shown) that may be used to provide the fluid to the ophthalmic surgical tool 112 or the surgical site. In some examples, the fluid outflow interface 212 may include a valve 213 to prevent fluid from exiting the bag 202 while the fluid-filled bag 202 is transported and stored. The fluid outflow interface 212 may be structurally configured to connect with the fluid infusion line in a sealed manner such that fluid may flow from the bag 202 through the infusion line. After the bag 202 is connected to the fluid infusion line, the valve 213 may be opened to allow fluid to flow out of the fluid outflow interface 212.

The bladder 204 is an inflatable structure configured to apply pressure on the bag 202. In the present example, the bladder 204 includes a plurality of chambers 208-1, 208-2, 208-3, 208-4 separated by a plurality of dividers 206-1, 206-2, 206-3. For example, the divider 206-1 is disposed between and separates chambers 208-1 and 208-2. The divider 206-2 is disposed between and separates chambers 208-2 and 208-3. The divider 206-3 is disposed between and separates chambers 208-3 and 208-4. In the example shown in FIG. 2, the chambers are arranged in a vertically stacked manner.

The bladder 204 also includes a pressure inlet 210 structurally configured to connect to a pressure source (not shown) through a pressure line (not shown). For example, after the bladder is disposed appropriately within a fluid delivery system such as the fluid delivery system 110 of FIG. 1, the pressure inlet 210 may be placed in fluid communication with to a pressure line that carries a fluid, such as a gas, from the pressure source. Thus, the bladder 204 may be inflated with a fluid from the pressure source.

The dividers 206-1, 206-2, 206-3 may be configured to allow a fluid to pass through in response to the fluid differential between adjacent chambers being above a threshold level. For example, the first divider 206-1 may be configured to allow fluid to pass through once the pressure level in the first chamber 208-1 reaches a threshold pressure level. After pressurized fluid begins to fill the top chamber 208-1, the pressurized fluid will not start to fill the second chamber 208-2 until pressure in the first chamber 208-1 reaches the threshold level. Similarly, the pressurized fluid will not begin to fill the third chamber 208-3 until the pressure level in the second chamber 208-2 reaches a threshold level based on the second divider 206-2. Likewise, the pressurized fluid will not begin to fill the fourth chamber 208-4 until the pressure level in the third chamber 208-3 reaches a threshold level based on the third divider 206-3. In this manner, the first chamber 208-1 will apply pressure on the bag 202 first, followed by the remaining chambers 208-2, 208-3, 208-4 successively. This helps to squeeze the bag 202 from the top down towards the fluid outflow interface 212 at the bottom of the bag 202. This helps prevent the bag 202 from being pinched in the middle to trap fluid within the upper portion of the bag 202.

In some examples, the dividers 206-1, 206-2, 206-3 may include check valves that regulate flow between adjacent chambers. The check valves may be structurally configured to allow fluid to pass through only if a certain threshold pressure differential between adjacent chambers is present. In some examples, the dividers 206-1, 206-2, 206-3 may be semipermeable membranes. Such membranes may be structurally configured to allow fluid to pass only at certain pressure levels. In some examples, each of the dividers 206-1, 206-2, 206-3 may have a similar threshold level. For example, each divider may have a pressure threshold of 3 pounds per square inch (PSI). In some examples, each of the dividers 206-1, 206-2, 206-3 may have different threshold levels. The different threshold levels may increase for lower dividers. For example, the first divider 206-1 may have a threshold level of 2 PSI, the second divider 206-2 may have a threshold level of 3 PSI, and the third divider 206-3 may have a threshold level of 4 PSI. Alternatively, the first divider 206-1 may have a threshold level of 4 PSI, the second divider 206-2 may have a threshold level of 3 PSI, and the third divider 206-3 may have a threshold level of 2 PSI.

In some examples, the dividers may include various sized orifices that allow fluid to flow through at various rates. For example, the second divider 206-2 may have a smaller orifice than the first divider 206-1. Similarly, the third divider 206-3 may have a smaller orifice than the second divider 206-2. In such a configuration, fluid being injected into the pressure inlet will fill the upper chambers faster than the lower chambers. The threshold pressure levels of each of the dividers 206-1, 206-2, 206-3 may be tuned to cause the bladder 204 to inflate as desired to cause the desired pressure on the bag 202. Threshold pressure levels other than the ones illustrated are contemplated as well. In some examples, threshold pressure levels may be selected to be between 1 PSI and 15 PSI. Yet others, higher and lower, are also contemplated. Various design factors may affect the selection of threshold pressure levels such as the pressure level of the pressure source, the materials forming the bladder 204, the materials forming the bag 202, as well as the size and shape of the bladder 204 and bag 202.

In some examples, the size or volume of each of the chambers 208-1, 208-2, 208-3, 208-4 may be similar. In some examples, however, the size or volume of each of the chambers 208-1, 208-2, 208-3, 208-4 may be different. For example, the first chamber 208-1 may be larger than the second chamber 208-2, which may be larger than the third chamber 208-3, which may be larger than the fourth chamber 208-4. The size of the chambers 208-1, 208-2, 208-3, 208-4 may be selected based on the desired manner of inflating the bladder 204 to provide the desired pressure on the bag 202. In the example shown, the bladder 204 has a vertical shape that tapers the chamber 208-1 to the chamber 208-4. As such, the bladder 204 may appear to be wedge-shaped when inflated. The tapered or wedge-shape may provide consistent pressure application to the bag 202.

In some examples, the bladder 204 and the bag 202 may be secured to each other through any of a variety of connector mechanisms. In some examples, the bladder 204 and the bag 202 may include connector mechanisms such as hook and loop straps, clips, buttons, or other connector mechanisms. Depending upon the connector mechanism, the bladder 204 may be readily disconnected from the bag 202. In some examples, the bladder 204 may be reusable. Thus, after a surgical procedure, used bag 202 may be disconnected from the bladder 204 and a new bag 202 may be connected to the bladder 204 before a subsequent surgical procedure. In other embodiments, the bladder 204 and the bag 202 are not connected, but are merely disposed adjacent to each other.

In some embodiments, the bladder 204 may be toroid shaped or otherwise shaped to receive the bag therein. In such embodiments, the bladder 204 may surround the exterior portion of the bag 202, and may cooperate with the bag 202 to force fluid from the bag to the infusion line.

Figure 3A:
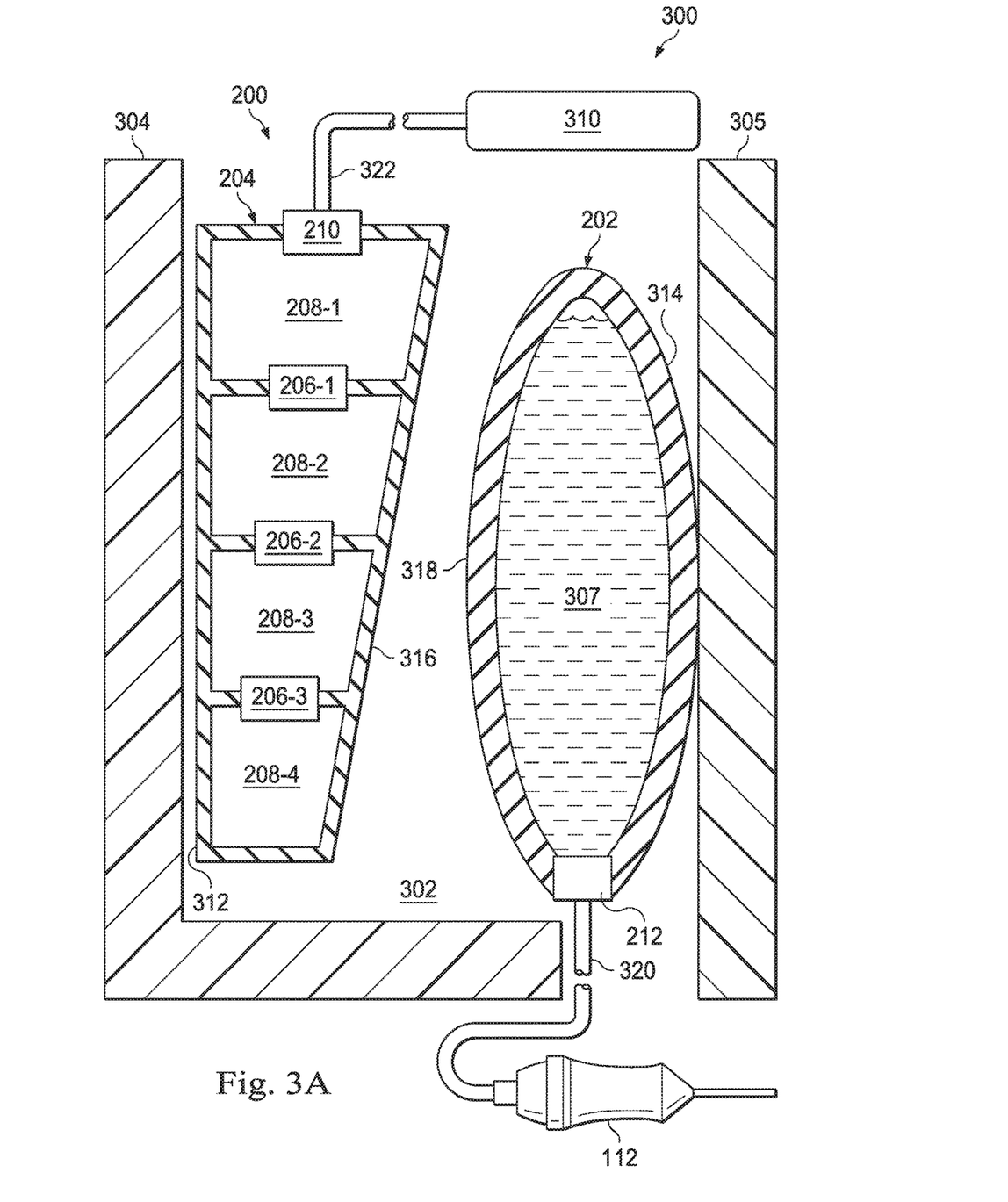
FIGS. 3A and 3B are diagrams showing the pressurizable fluid supply apparatus disposed within a fluid delivery system.
Figure 3B:
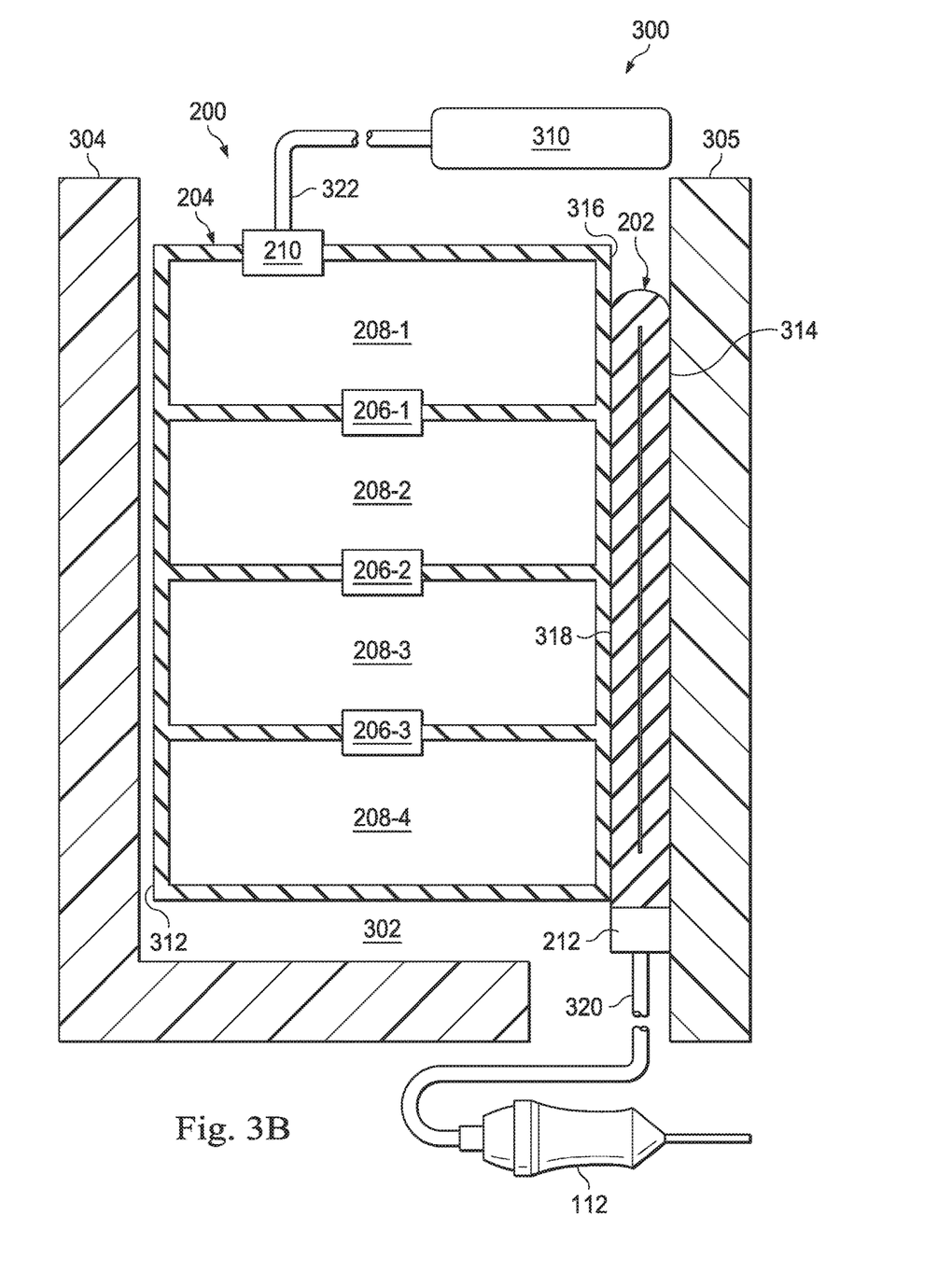

FIGS. 3A and 3B are diagrams showing the pressurizable fluid supply apparatus 200 placed within a fluid delivery system 300. The fluid delivery system 300 may be the same system as the fluid delivery system 110 in FIG. 1. FIG. 3A illustrates the pressurizable fluid supply apparatus 200 before the bladder 204 is inflated (e.g., with bladder 204 in a first primarily deflated condition. According to the present example, the pressurizable fluid supply apparatus 200 is introduced to the fluid delivery system 300. Here, the pressurizable fluid supply apparatus 200 is disposed in an appropriate receptacle 302. The pressurizable fluid supply apparatus 200 may then be connected with the fluid delivery system 300 by connecting the pressure inlet 210 of the bladder 204 to a pressure source 310 via the pressure line 322. The fluid outflow interface 212 of the bag 202 may also be connected to a fluid infusion line 320 that is in fluid communication with an ophthalmic surgical tool 112.

In some implementations, the pressure source 310 may be a replaceable canister of compressed gas that is inserted into the surgical console (e.g., 100, FIG. 1). In some examples, the pressure source 310 may be provided by a separate machine that is connectable to the console through a pressure line, such as a compressor. In either case, a pressure line 322 within the surgical console connect the pressure source 310 to the pressure inlet 210 and delivers pressurized fluid from the pressure source 310 to the pressure inlet 210.

The fluid infusion line 320 may extend between and connect the fluid outflow interface 212 with the ophthalmic surgical tool 112. All or a part may be flexible to provide mobility to the ophthalmic surgical tool 112. Such a flexible fluid line may provide a connection between the surgical console and the ophthalmic surgical tool 112. In some examples, the fluid infusion line 320 may connect directly to the ophthalmic surgical tool for a single fluid infusion line 320. In other examples, the fluid infusion line 320 may include rigid segments as well as flexible segments. In some embodiments, rigid segments may be carried on the console, while flexible segments extend from the console to the ophthalmic surgical tool 112.

The receptacle 302 in which the pressurizable fluid supply apparatus 200 is placed within the fluid delivery system 300 may be surrounded by physical structures such as rigid or unyielding walls 304, 305 such that inflation of the bladder 204 causes expansion that squeezes the bag 202 between the bladder 204 and a wall 305. The walls 304, 305 may be fixed with respect to the fluid delivery system 300 such that inflation of the bladder 204 does not move the walls 304, 305 but instead squeezes the bag 202, increasing the pressure of the fluid therein and causing the fluid to flow through the infusion line at a desired rate. Specifically, inflation of the bladder 204 causes a first wall 312 of the bladder 204 to press up against the wall 304. Additionally, a second wall 316 of the bladder 204 presses up against a first wall 318 of the bag 202. Inflation of the bladder 204 this causes a second wall 314 of the bag 202 to press up against the wall 305. Thus, as the bladder 204 inflates, the fluid 307 is pressed out of the bag 202 through the fluid outflow interface 212.

FIG. 3B illustrates the pressurizable fluid supply apparatus 200 after the bladder 204 has been inflated and after fluid has been forced from the bag 202 through the fluid outflow interface 212. As illustrated, each of the chambers 208-1, 208-2, 208-3, 208-4 of the bladder are filled such that their volume has filled the receptacle 302 and they press up against the bag 202. Here, the bladder 204 is in a second substantially inflated condition. When the bladder 204 is fully inflated is shown, the fluid 307 that was within the bag 202 has been emptied from the bag 202 through the fluid outflow interface 212.

Figure 4:
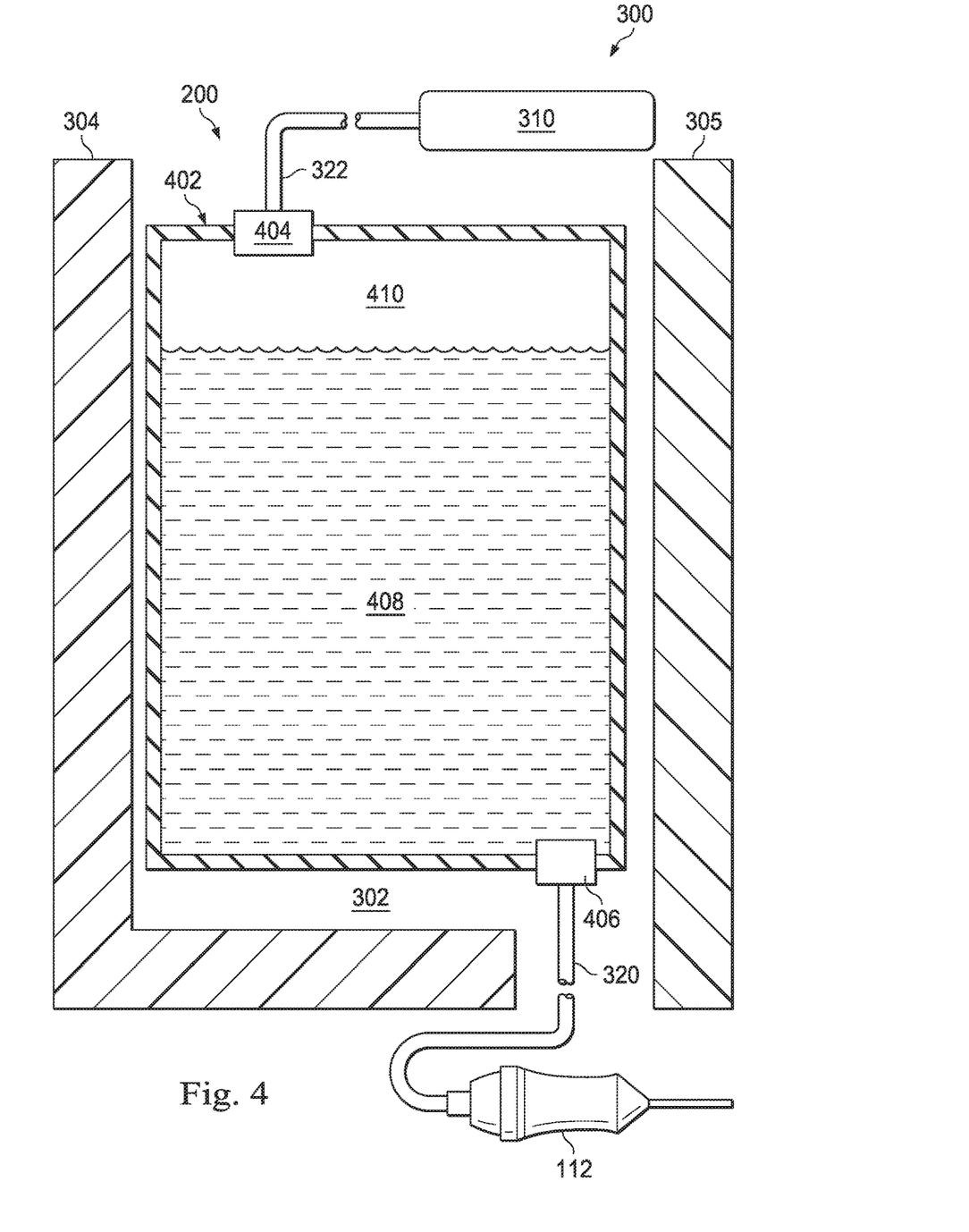
FIG. 4 is a diagram showing an illustrative bottle disposed within the fluid delivery system.

FIG. 4 is a diagram showing illustrative bottle 402 disposed within the fluid delivery system 300. While the bottle 402 is shown as housed inside the console, in some examples, the bottle 402 may be hung adjacent to the console. Since the 300 is the same as described in FIG. 3, it should be apparent that the pressurizable fluid supply apparatus 200 may be a replacement for a bottle. FIG. 4 shows the bottle 402 disposed within a system structurally configured for use with a bottle 402. The bottle 402 may include a chamber 410 for holding fluid 408, a pressure inlet 404, and a fluid outflow interface 406. The bottle 402 may be a glass or polymer bottle having substantially non-inflatable sides, such that the volume remains relatively consistent when pressurized.

The pressure inlet 404 of the bottle 402 may have a similar shape or structure as the pressure inlet 210 of the pressurizable fluid supply apparatus 200. In some examples, the pressure inlet 210 is a quick disconnect connector or a lure fitting. Thus, the pressure inlet 404 of the bottle 402 is connectable to the pressure source 310 through the pressure line 322. In some examples, however, the pressure inlet 404 of the bottle 402 may be different than the pressure inlet 210 of the pressurizable fluid supply apparatus 200. In such a case, an adapter may be used to make either the pressurizable fluid supply apparatus 200 or the bottle 402 compatible with the pressure line 322.

Similarly, the fluid outflow interface 406 of the bottle 402 may have a structure or shape similar to the fluid outflow interface 212 of the pressurizable fluid supply apparatus 200. Thus, the fluid outflow interface 406 of the bottle 402 is connectable to the fluid infusion line 320. In some examples, however, the fluid outflow interface 406 of the bottle 402 may be different than the fluid outflow interface 212 of the pressurizable fluid supply apparatus 200. In such a case, an adapter may be used to make either the pressurizable fluid supply apparatus 200 or the bottle 402 compatible with the fluid infusion line 320.

Figure 5:
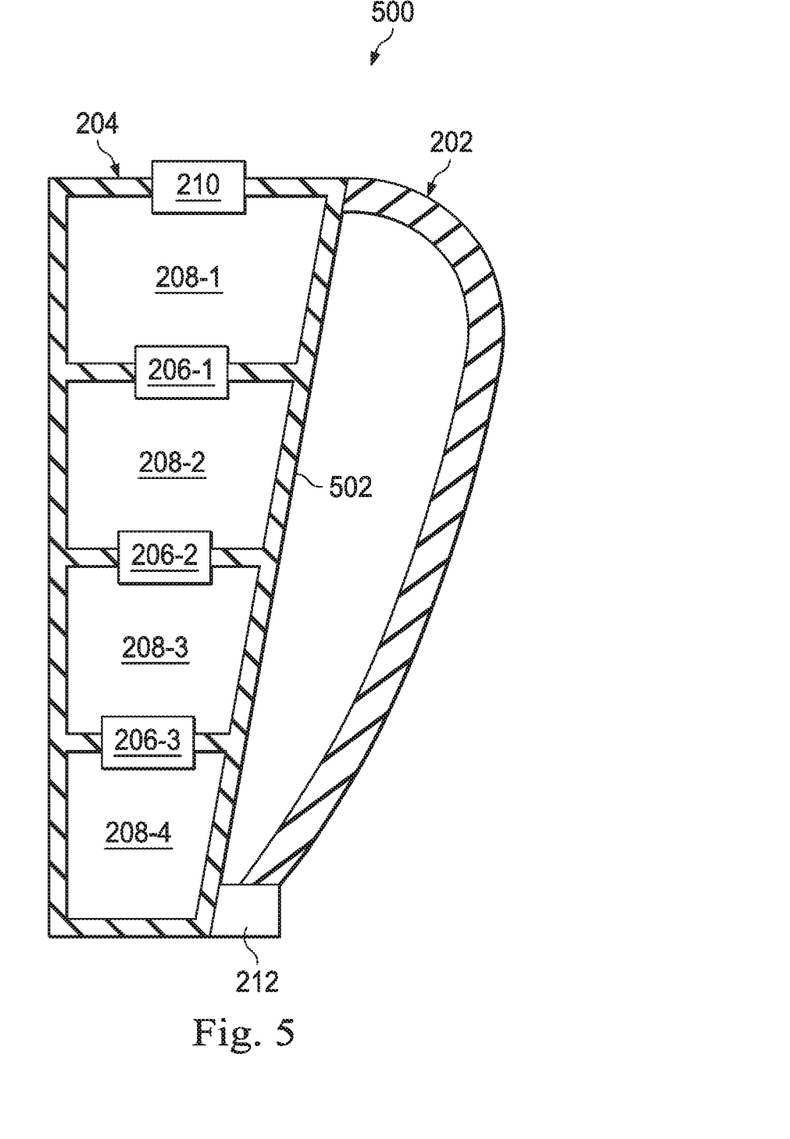
FIG. 5 is a diagram showing an illustrative pressurizable fluid supply apparatus in which the bag and the bladder share a wall.

To inject fluid 408 into the fluid infusion line 320, a pressurized fluid, such as a gas, is introduced from the pressure source 310 through the pressure inlet 404 and into the chamber of the bottle 402. Instead of inflating a bladder as described with reference to FIGS. 3A and 3B, the pressure source, fills the bottle 402 with the gas. Because of the relatively fixed volume of the bottle 402, this pushes the fluid 408 out of the fluid outflow interface 406. Thus, the fluid delivery system 300 is capable of supporting a bottle 402 and a pressurizable fluid supply apparatus 200 without the use of an actuator mechanism. In other words, because the bag 202 of the pressurizable fluid supply apparatus 200 is squeezed by the bladder 204, the pressurizable fluid supply apparatus 200 is operable without use of the actuator mechanisms used in conventional bag-based fluid delivery systems. FIG. 5 is a diagram illustrating an example pressurizable fluid supply apparatus in which the bag and the bladder share a wall. According to the present example, the delivery bag apparatus 500 is a single, integrated structure that includes both the bladder 204 and the bag 202. In other words, the bag 202 shares a wall 502 with the bladder 204. More specifically, each chamber 208-1, 208-2, 208-3, 208-4 within the bladder 204 shares the wall 502 with the bag 202. When inflated, the bladder 204 and the bag 202 to cooperate to provide fluid flow in the manner described above.

Figure 6:
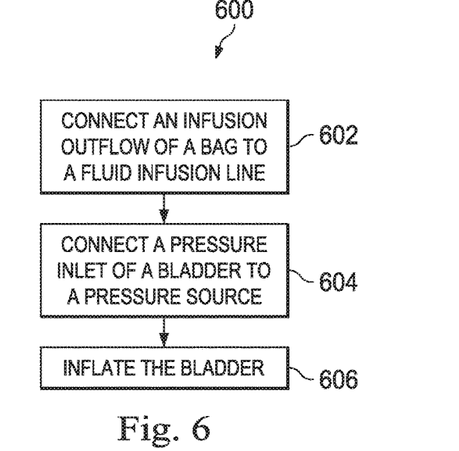
FIG. 6 is a flowchart showing an illustrative method for providing fluid to a patient's eye through use of a pressurizable fluid supply apparatus within a fluid delivery system.

FIG. 6 is a flowchart showing an illustrative method for providing fluid to a patient's eye through use of a pressurizable fluid supply apparatus. According to the present example, the method 600 includes a step 602 for connecting a fluid outflow interface (e.g., 212, FIG. 2) of a fluid-filled bag to a fluid infusion line (e.g. 320, FIG. 3) of a fluid delivery system (e.g., 300, FIG. 3). The bag may correspond to the bag 202 of the pressurizable fluid supply apparatus 200 described above. As described above, the fluid infusion line may connect to the fluid outflow interface. The fluid infusion line may provide fluid communication between the bag and an ophthalmic surgical tool (e.g., 112, FIG. 1).

At 604, a user connects a pressure inlet (e.g. 210, FIG. 2) of a bladder (e.g. 204, FIG. 2) to a pressure source (e.g. 310, FIG. 3). As described above, the bladder may be an inflatable structure that is structurally configured to be inflated to incrementally apply pressure on the fluid-filled bag. The bladder 204 may include a plurality of chambers (e.g., 208-1, 208-2, 208-3, 208-4) separated by a plurality of dividers (206-1, 206-2, 206-3). The bladder 204 also includes a pressure inlet 210. The dividers are configured to selectively allow fluid flow between the chambers under specified conditions. Such conditions may be, for example, pressure within one chamber above a threshold level, such as 3 PSI. In other words, the dividers selectively allow fluid to pass through because fluid is prevented from passing at certain pressure differentials and allowed to pass at other pressure differentials. For example, as described above, the dividers may be check valves or semipermeable membranes structurally configured to allow fluid flow there through when the pressure on one side of the divider reaches a predefined threshold level.

At 606, the bladder (e.g., 204, FIG. 2) inflates. In some examples, the bladder is inflated using the pressure source. As the volume of the bladder increases, it applies pressure on the bag, pressurizing the fluid and regulating the flow from the bag. The bladder is inflated in a manner such that the bladder presses the bag against a wall to press fluid from the bag into the fluid infusion line. The pressurizable fluid supply apparatus as described herein is compatible with a fluid delivery system (e.g., 300, FIG. 3) that is also suitable for using bottles as a fluid delivery mechanism. For example, a bottle (e.g., 402) may be disposed within the fluid delivery system 300 instead of the pressurizable fluid supply apparatus 200. The pressure inlet (e.g. 404, FIG. 4) of the bottle may be connected to the pressure source and the fluid outflow interface (e.g., 406, FIG. 4) of the bottle may be connected to the fluid infusion line. Then, the bottle can be pressurized through use of the pressure source to push the fluid out of the bottle at a desired flow rate. Again, the flow rate may be controlled by the control system to provide the desired fluid flow to the patient's eye.

Although described having four chambers, other embodiments of the bag include two chambers, three chambers, or more than four chambers.

The pressurizable fluid supply apparatus as described herein may also be used with fluid delivery systems that have an actuator mechanism to squeeze the bag. In such cases, both the bladder and the bag may be placed within such a fluid delivery system. The actuator mechanism may then squeeze the bladder and bag without inflating the bladder to press fluid out of the bag. Persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A pressurizable fluid supply apparatus for supplying an infusion fluid during a surgical treatment, the pressurizable fluid supply apparatus comprising:
    a bag to hold the infusion fluid, the bag comprising a fluid outflow interface;
    an inflatable bladder positioned adjacent to the bag, the inflatable bladder being fillable to inflate from a first condition having a first volume to a second condition having a second volume, the inflatable bladder comprising:
    a plurality of chambers positioned in series, each successive chamber of the plurality of chambers being smaller in size than the immediately preceding chamber; adjacent chambers being separated by dividers, the dividers configured to selectively allow fluid flow between adjacent chambers, such that each successive chamber of the plurality of chambers fills after a pressure in the preceding chamber reaches a threshold, thereby squeezing the bag in a controlled manner from a first end of the bag to a second end of the bag; and a pressure inlet positioned at a top of the inflatable bladder.

2. The pressurizable fluid supply apparatus of claim 1, wherein the dividers comprise check valves.

3. The pressurizable fluid supply apparatus of claim 1, wherein the dividers comprise semipermeable membranes.

4. The pressurizable fluid supply apparatus of claim 1, wherein a wall of the inflatable bladder is attached to a wall of the bag.

5. The pressurizable fluid supply apparatus of claim 1, wherein the inflatable bladder and the bag share a same wall.

6. The pressurizable fluid supply apparatus of claim 1, wherein the pressurizable fluid supply apparatus is configured to be disposed within a receptacle of a fluid delivery system such that opposing sides of the inflatable bladder and bag are disposed between fixed walls.

7. The pressurizable fluid supply apparatus of claim 6, wherein the fluid outflow interface is connectable to a fluid infusion line that is in fluid communication with a tool for insertion into a patient's eye.

8. The pressurizable fluid supply apparatus of claim 6, wherein the pressure inlet is connectable to a pressure source.

9. A fluid delivery system comprising:
a pressure source;
a fluid infusion line;
a pressurizable fluid supply apparatus comprising:
a bag to hold a fluid, the bag comprising a fluid outflow interface that is connectable to the fluid infusion line;
a bladder positioned adjacent to the bag, the bladder comprising:
a plurality of chambers positioned in series, each successive chamber of the plurality of chambers being smaller in size than the immediately preceding chamber; adjacent chambers of the plurality of chambers being separated by dividers configured to selectively allow fluid flow between adjacent chambers, such that each successive chamber of the plurality of chambers fills after a pressure in the preceding chamber reaches a threshold, thereby squeezing the bag in a controlled manner from a first end of the bag to a second end of the bag; and
a pressure inlet positioned at a top of the bladder, the pressure inlet being connectable to the pressure source; and
a receptacle adapted to receive the pressurizable fluid supply apparatus.

10. The fluid delivery system of claim 9, wherein the apparatus is sized and shaped to be disposed within the receptacle such that opposing sides of the bladder and the bag are disposed between walls.

11. The fluid delivery system of claim 10, wherein the receptacle is sized and shaped such that inflation of the bladder presses the bag against at least one of the walls such that fluid is pressed out of the bag through the fluid outflow interface.

12. The fluid delivery system of claim 11, wherein at least two of the plurality of chambers are sized differently, with a larger sized chamber positioned above a smaller sized chamber.

13. A method comprising:
connecting a fluid outflow interface of a fluid-filled bag to a fluid infusion line;
connecting a pressure inlet of a bladder to a pressure source, the bladder comprising a plurality of chambers positioned in series, adjacent chambers being separated by dividers, each successive chamber of the plurality of chambers being smaller in size than the immediately preceding chamber; the dividers configured to selectively allow fluid flow between adjacent chambers, such that each successive chamber of the plurality of chambers fills after a pressure in the preceding chamber reaches a threshold, thereby squeezing the bag in a controlled manner from a first end of the bag to a second end of the bag; and
with fluid from the pressure source, inflating the bladder such that the bladder presses the fluid-filled bag against a wall to press fluid from the bag into the fluid infusion line.

14. The method of claim 13, wherein the dividers comprise at least one of: check valves and semipermeable membranes.

* * * * *